United States Patent
Hickey et al.

(10) Patent No.: US 9,464,302 B2
(45) Date of Patent: Oct. 11, 2016

(54) METHODS FOR SUSTAINING THE VIABILITY OF ACETOGENS DURING A DECREASE OR CESSATION OF SYNGAS FLOW

(71) Applicant: Coskata, Inc., Warrenville, IL (US)

(72) Inventors: Robert Hickey, Okemos, MI (US); Andrew Reeves, Chicago, IL (US)

(73) Assignee: Synata Bio, Inc., Warrenville, IL (US)

( * ) Notice: Subject to any disclaimer, the term of this patent is extended or adjusted under 35 U.S.C. 154(b) by 99 days.

(21) Appl. No.: 14/327,165

(22) Filed: Jul. 9, 2014

(65) Prior Publication Data

US 2016/0010118 A1    Jan. 14, 2016

(51) Int. Cl.
| | |
|---|---|
| *C12P 7/06* | (2006.01) |
| *C12N 1/00* | (2006.01) |
| *C12P 7/16* | (2006.01) |
| *C12P 7/04* | (2006.01) |
| *C12N 1/20* | (2006.01) |

(52) U.S. Cl.
CPC . *C12P 7/16* (2013.01); *C12N 1/20* (2013.01); *C12P 7/04* (2013.01); *C12P 7/065* (2013.01); *Y02E 50/10* (2013.01); *Y02E 50/17* (2013.01)

(58) Field of Classification Search
CPC ............. C12P 7/16; C12P 7/14; C12P 7/065; C12P 7/06; C12P 7/04; C12N 1/20; C12N 1/04
See application file for complete search history.

(56) References Cited

U.S. PATENT DOCUMENTS 9,034,618 B2 *   5/2015   Adams et al. ................ 435/161

* cited by examiner

*Primary Examiner* — Kara Johnson
(74) *Attorney, Agent, or Firm* — Cardinal Law Group

(57) ABSTRACT

The methods are disclosed for sustaining a population of microorganisms in an aqueous fermentation broth used in a process to convert syngas to alcohol when the supply of syngas is decreased or ceased. The methods involve supplying at least one reducible anion in a rate an amount sufficient to maintain the population of microorganisms.

7 Claims, No Drawings

METHODS FOR SUSTAINING THE VIABILITY OF ACETOGENS DURING A DECREASE OR CESSATION OF SYNGAS FLOW

FIELD OF THE INVENTION

This invention pertains to methods for sustaining the viability of acetogens used for the bioconversion of syngas to alcohol in the event of a decrease or cessation of syngas flow, and more particularly in one aspect to methods that are pH self-regulating and in another aspect to methods that reduce the metabolic rate of the acetogens.

BACKGROUND

Anaerobic fermentations of hydrogen and carbon monoxide involve the contact of the substrate gas in an aqueous fermentation menstruum with microorganisms capable of generating alcohols such as ethanol, propanol, i-butanol and n-butanol. The production of these alcohols requires significant amounts of hydrogen and carbon dioxide and/or carbon monoxide. For instance, the theoretical equations for the conversion of carbon monoxide and hydrogen to ethanol are:

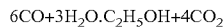

$$6CO + 3H_2O \cdot C_2H_5OH + 4CO_2$$

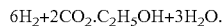

$$6H_2 + 2CO_2 \cdot C_2H_5OH + 3H_2O.$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Typically the substrate gas for carbon monoxide and hydrogen conversions is, or is derived from, a synthesis gas (syngas) from the gasification of carbonaceous materials, partial oxidation or reforming of natural gas and/or biogas from anaerobic digestion or landfill gas or off-gas streams of various industrial methods such as off gas from coal coking and steel manufacture. The substrate gas contains carbon monoxide, hydrogen, and carbon dioxide and usually contains other components such as water vapor, nitrogen, methane, ammonia, hydrogen sulfide and the like.

These anaerobic fermentation processes are suitable for continuous processes. The syngas is passed into a bioreactor the aqueous fermentation broth for the bioconversion. Off gases can be removed from the bioreactor, and aqueous broth can be withdrawn from the bioreactor for recovery of the oxygenated organic compound at a rate sufficient to maintain steady-state operation. For such processes to be commercially viable they must be able to benefit from the advantages of scale, and thus facilities using these processes need to be able to produce upwards of 50 or 100 million or more gallons of oxygenated organic compound per year. These anaerobic fermentation processes necessarily involve the mass transfer of substrate from the gas phase into the liquid phase for access by the microorganisms. These mass transfer considerations together with economies of scale, tend to favor the use of large reactors for commercial-scale facilities. Hence, commercial scale reactors, i.e., those with liquid capacities of at least 1 million, and more often at least about 5, say, 5 to 25, million, liters would be advantageous.

The start-up of these commercial-scale facilities can be problematic due to the large volume of microorganisms required and the time required to grow a sufficient population of the microorganisms. The microorganisms for the anaerobic fermentation typically are expected to be generated by seed farms at the site of the facility. The capital and operating expense for a seed farm is not insignificant. Usually the seed farms are comprised of a sequential series of reactors of increasing size with the final reactor having enough volume to provide an initial charge to the commercial-scale reactor. Usually, the growth in each seed farm stage is targeted to increase the size of the population by a factor of 10 and each stage usually takes from 2 to 7 days to achieve the sought growth. Once charged from the seed farm, the reactor is then operated to promote the growth of the population of microorganisms while increasing the volume of the aqueous medium in the reactor until steady-state is achieved. U.S. Published Patent Application 20130078693 discloses processes for starting up and operation of deep tank anaerobic fermentation reactors.

The supply of syngas is subject to disruptions, both planned and unplanned. The microorganisms used for the bioconversion of syngas to alcohol have a limited period where viability can be retained after a cessation of flow of syngas. Under typical temperatures used for the bioconversion, the microorganisms quickly lose viability, and a loss of syngas for a period of 24 hours will result in at least about 90 percent of the population of microorganisms being killed. Reestablishing the population of microorganisms after such a decrease or cessation of syngas flow requires time, and during this time alcohol is not being produced at the sought rates. Thus, it is important for a commercial-scale facility to be able to substantially maintain as viable the population of microorganisms during any period where the syngas feed is materially decreased or ceased. Any method for maintaining the viability of the population of microorganisms should be effective for at least the most frequent duration of impaired syngas supply, which is typically at least about 6 hours, and more often at least about 12 to 24 hours, and potentially for several days to a week. It is axiomatic that any such method be able to be quickly implemented to minimize damage to the population of microorganisms. Moreover, the method itself should not induce unduly adverse effects on the microorganisms. Further, the method should not unduly hinder resumption of, or otherwise adversely affect, the normal operations once the impairment of the syngas supply has been alleviated, and the method should be economically viable to implement on a commercial-scale facility.

One option is to introduce sugar into the fermentation broth as substrate for the microorganisms in the event of a syngas feed interruption. This option would increase the risk of microbial contamination since it provides an environment conducive to the growth of a wide variety of microorganisms. It also would result in the generation of free (un-ionized) acid that requires the addition of alkalinity to avoid killing the microorganisms. For instance, one mole of fructose would yield three moles of acetic acid.

Adams, et al., in United States Patent Application Publication 2010/0227377 A1 propose adding carbon dioxide during periods of decrease or ceased syngas flow to a fermentation broth used to produce ethanol. They postulate that carbon dioxide and ethanol serve to provide energy back to the culture to maintain viability. The method disclosed by Adams, et al., is not without challenges. First, the method requires the introduction of carbon dioxide into the fermentation reactor. The dissolved concentration is dependent upon the gas transfer rate and uptake by the microorganisms and thus is difficult to control. Second, the metabolic reaction results in the production of acetic acid. This can result in a significant accumulation of free (un-ionized) acids in the fermentation reactor. The acidity must therefore be addressed by the addition of an alkalinity source, but the build-up of the cation associated with the alkalinity source can reach inhibitory levels. Moreover, the patent applicants do not disclose methods for maintaining the redox potential of the fermentation broth suitable for restart of the syngas fermentation once the flow of syngas can be restored.

Frostl, et al, in "Effect of nitrate on the autotrophic metabolism of the acetogens *Clostridium thermoautotrophicum* and *Clostridium thermoaceticum*, J. of Bacteriology, 1996, 178(15), pages 4597 to 4603, demonstrated the effect of nitrate anion on the growth and product profiles of the subject acetogens in the presence of a carbon dioxide feed. A variety of substrates were used by the authors with and without nitrate anion. Their summary states in part:

> "Although nitrate stimulated the capacity of *Clostridium thermoautotrophicum* and *Clostridium thermoaceticum* to oxidize (utilize) substrates under heterotrophic conditions, it inhibited autotrophic $H_2$—$CO_2$-dependent growth." .... "Nitrate has no appreciable effect on the specific activities of enzymes central to the acetyl-coenzyme A (CoA) pathway. However, membranes obtained from cells cultivated under nitrate-dissimilating conditions were deficient in the b-type cytochrome that was typical of membranes from acetogenic cells, i.e., cells dependent upon the synthesis of acetate for the conservation of energy." ....

Accordingly, improved methods are sought to maintain a viable microorganism population in a fermentation broth during periods of decreased or ceased syngas feed.

SUMMARY

By the methods of this invention the viability of a population of microorganisms being used for the bioconversion of syngas to alcohol can be sustained in the event of a decrease or cessation of the supply of syngas (impairment of syngas supply) to the aqueous fermentation broth by supplying to the broth limited, but sufficient, amounts of at least one reducible nitrogen or sulfur-containing anion (herein referred to as reducible anion) to substantially maintain the microorganism population. The reducible anion serves as an electron sink to enable the microorganism to bioconvert alcohol in the broth. Reducible nitrogen and sulfur-containing anions include nitrate, sulfite, bisulfite, thiosulfate and metabisulfite anions. The limited, but sufficient, amounts of the at least one reducible anion are amounts that result in a concentration of the reducible anion that does not adversely affect the microorganisms but maintains the viability of the population of microorganisms.

If desired, the methods of this invention can be implemented while retaining the aqueous fermentation broth in the bioreactor used for the syngas bioconversion. Advantageously the supply of the nitrate anion to the fermentation broth is capable of being controlled with good precision as no gas to liquid mass transfer is involved. Consequently, the rate of addition of nitrate anion can be meted at the rate that the microorganisms are capable of bioconverting the nitrate anion. Moreover, the reducible anion can be quickly dispersed within the aqueous fermentation broth, even where commercial scale bioreactors are used, to make the reducible anion immediately available to the microorganisms. Thus, the methods of this invention can be implemented quickly in the event of an impairment in syngas supply to attenuate loss of viability of the population of microorganisms.

It should be understood that it is not essential for the entire population of microorganisms to survive for a method to sustain the viability of the population of microorganisms. The objective is to maintain sufficient populations of microorganisms such that upon resumption of the syngas feed, full production rates can promptly be achieved. At a population of 25 percent of the sought population, only two doublings of viable microorganisms are required which typically can be accomplished for most microorganisms in less than about 36 hours, and sometimes in less than about 18 hours.

Further, it is possible to practice the methods without the generation of free (un-ionized) acid that would require supplying alkalinity to the fermentation broth which would cause a build-up of the cation associated with the source of alkalinity. Accordingly, the methods of this invention also enable the maintenance of oxidation reduction potentials in the fermentation broth that are conducive for proper functioning of the microorganisms.

Without wishing to be limited by theory, it is believed that sustenance of the microorganisms where the nitrate anion is the reducible anion and is supplied by sodium nitrate and ethanol is the alcohol that was being produced by the microorganisms and is thus present in the aqueous fermentation broth, involves metabolic reactions that can be summarized as follows:

$$Na^+ + NO_3^- + 4H_2 \rightarrow Na^+ + 2OH^- + H_2O + NH_4^+$$

$$2CH_3CH_2OH + 2H_2O \rightarrow 2CH_3COO^- + 4H_2 + 2H^+$$

which results in the net reaction of:

$$Na^+ + NO_3^- + 2CH_3CH_2OH \rightarrow 2CH_3COO^- + Na^+ + H_2O + NH_4^+.$$

Advantageously, the energy yield provided by the reduction of the reducible anion, especially nitrate, is substantial, and therefor little needs to be used to sustain the viability of the population of microorganisms. Consequently, little alcohol needs to be consumed. Thus the methods of this invention can be implemented for extended periods of time without undue build-up of carboxylate salt (e.g., acetate and sodium) or pH increase.

It should be understood that the reduction of the nitrate anion can result in nitrite and nitrogen dioxide being present. However, the limited supply of reducible anion, in the case of nitrate, favors the essentially complete reduction of nitrate to ammonium cation. Where the reducible anion is a sulfur-containing anion, hydrogen sulfide is a product. The use of sulfur-containing reducible anions would result in hydrogen sulfide being evolved from the aqueous fermentation broth. Accordingly, unit operations to address hydrogen sulfide emissions are usually desirable. As can be readily appreciated, the methods 4 of this invention result in an additional benefit, namely the production of ammonium cation or hydrogen sulfide that can be used as a nutrient by the microorganisms.

By limiting the supply of reducible anion, it is believed that the metabolic rate in the microorganisms can be reduced thereby both reducing the rate of cell reproduction and the energy flux required to sustain a cell. Consequently, the temperature of the aqueous fermentation broth need not be lowered as the only means to reduce metabolic rate. This rate reduction has the additional benefit of enabling the residual alcohol in the aqueous fermentation broth at the time of the impairment of the syngas supply to sustain the microorganisms for more extended durations and thus reduce the need to externally supply one or more alcohols as electron providers for the microorganism. The methods of this invention do not require the presence of any normally gaseous substrate such as carbon dioxide to be added to fermentation broth.

The methods of this invention enable a quick transition to normal operations for the bioconversion of syngas upon the cessation of the impairment of syngas supply. The limited concentrations of reducible anion are not sufficient to inhibit the metabolic pathways for the hydrogen conversion or carbon monoxide conversion of the syngas or otherwise adversely affect the microorganisms. The aqueous fermentation broth can be maintained at about the sought temperature for the syngas bioconversion during the impairment of syngas supply while retaining viability of the population of microorganisms. Hence the time to achieve a temperature ramp-up can be avoided.

The methods of this invention are particularly useful where the duration of the decrease or cessation of syngas is anticipated to be relatively short. Nevertheless, as the supply of reducible anion can be effectively metered to achieve a population of microorganisms residing at a reduced metabolic state, more extended impairments in syngas supply can be accommodated.

In one broad aspect this invention pertains to methods for sustaining a population of microorganisms for the bioconversion of syngas to alcohol contained in an aqueous fermentation broth in the event of a decrease or cessation of syngas feed to the fermentation broth being used for the bioconversion which broth contains said alcohol, which methods comprise continuously or intermittently adding during the period of decreased or ceased syngas feed at least one reducible anion selected from the group consisting of nitrate, sulfite, bisulfite, thiosulfate and metabisulfite anion, to the fermentation broth at a rate sufficient to substantially maintain the microorganism population by the bioconversion of alcohol to carboxylate anion and reduction of the at least one reducible anion. By this continuous or intermittent addition of the at least one reducible anion, ample amounts of the at least one reducible anion can be available to sustain the microorganisms while avoiding concentrations that would be adverse to the microorganisms. Where the flow of syngas ceases, it is believed that the Wood-Ljungdahl pathway in the microorganisms becomes inoperative, and therefore the at least one reducible anion would go towards respiration and not inhibition of the pathway. Where some flow of syngas continues, the at least one reducible anion, especially in the case of nitrate anion, can affect the Wood-Ljungdahl pathway, and thus the concentration at which adverse effects to the microorganism can occur is lower than that for complete cessation of the syngas supply.

Preferably a low concentration of the at least one reducible anion is maintained in the aqueous fermentation broth to conserve nitrate anion and enhance the economic viability of the methods of this invention. Frequently, the rate of addition of the at least one reducible anion is sufficient to maintain a substantially stable concentration of the at least one reducible anion in the aqueous fermentation broth. Thus, the rate of addition reflects the size of the population of the microorganisms and their metabolic activities. In many instances, the rate of addition of the at least one reducible anion is less than about 0.25 grams per hour per liter, and is sometimes in the range of between about 0.005 to 0.10, say, 0.01 to 0.05, grams per hour per liter of the aqueous fermentation broth.

In another broad aspect this invention pertains to methods for sustaining a population of microorganisms for the bioconversion of syngas to alcohol contained in an aqueous fermentation broth in the event of a decrease or cessation of syngas feed to the fermentation broth being used for the bioconversion which broth contains said alcohol, which methods comprise continuously or intermittently adding during the period of decreased or ceased syngas feed at least one reducible anion selected from the group consisting of nitrate, sulfite, bisulfite, thiosulfate and metabisulfite anion, to the fermentation broth at a rate sufficient to substantially maintain the microorganism population by the bioconversion of alcohol to carboxylate anion and reduction of the at least one reducible anion but below that which would provide a concentration of said at least one reducible anion that adversely affects the microorganism.

Preferably the at least one reducible anion comprises nitrate. In some instances it is desirable to also use at least one of sulfite, bisulfite, thiosulfate and metabisulfite anion in combination with the nitrate anion to help maintain desired redox potentials. The mode of operation takes advantage of the benefit of the sulfur-containing anion to maintain the desired redox potential and to supply sulfur nutrient without incurring the volume of hydrogen sulfide production if the sulfur-containing anion were the only reducible anion. By the continuous or intermittent addition of reducible anion the concentration of reducible anion in the aqueous fermentation broth need not exceed about 20, and is often less than about 10, and frequently less than about 5, milligrams per liter of broth. In preferred aspects of the invention the redox potential of the aqueous fermentation broth is maintained lower than about −200 or −230, and more preferably lower than about −250, millivolts to facilitate stabilizing the population of microorganisms. Often the redox potential is in the range of about −250 to −525, and sometimes in the range of about −300 to −450, millivolts. In many instances, the use of lower redox potentials facilitates the transition of the population of microorganisms to growth upon resumption of the syngas feed.

At the conclusion of the duration of decreased or ceased syngas feed, syngas can be introduced into the aqueous fermentation broth under bioconversion conditions. Preferably, the nitrate anion is reduced to less than about 2, preferably less than about 1, milligrams per liter prior to initiating the syngas feed to facilitate transition of the microorganisms to the syngas metabolism pathways. If the temperature of the aqueous fermentation broth was lowered to reduce metabolic activity, the temperature can be increased before or after the initiation of the syngas feed.

DETAILED DISCUSSION

All patents, published patent applications and articles referenced herein are hereby incorporated by reference in their entirety.

Definitions

As used herein, the following terms have the meanings set forth below unless otherwise stated or clear from the context of their use.

The use of the terms "a" and "an" is intended to include one or more of the element described.

Alcohol means one or more alkanols containing two to six carbon atoms. In some instances the alcohol is a mixture of alkanols produced by the microorganisms contained in the aqueous fermentation broth.

Aqueous broth, or aqueous fermentation broth, means a liquid water phase which may contain dissolved compounds including, but not limited to hydrogen, carbon monoxide, and carbon dioxide. The broth may, but is not required, to contain microorganisms.

A bioreactor assembly is an assembly of one or more vessels suitable to contain aqueous fermentation broth and microorganisms for the bioconversion and can contain associated equipment such as injectors, recycle loops, agitators, and the like.

A concentration of said at least one reducible anion that adversely affects the microorganism is where at least about 20 percent of the viable microorganisms in the aqueous fermentation broth suffer from an inhibition of the Wood-Ljungdahl pathway upon resumption of the syngas flow as determined in comparison with metabolic rate per liter of fermentation broth prior to the impairment of syngas supply, at substantially the same microorganism density, all other conditions being substantially the same.

Redox potential or oxidation reduction potential of the aqueous fermentation broth is measured in millivolts and is taken as the measurement of such value with reference to an aqueous solution measured against Ag/Ag—Cl type electrode utilizing a 3.8 M KCl electrolyte salt bridge.

Intermittently means from time to time and may be at regular or irregular time intervals.

Substantially maintain a population of microorganisms means that at least 25 percent of the microorganisms retain viability.

Syngas means a gas containing at least one of hydrogen and carbon monoxide and may, and usually does, contain carbon dioxide.

Overview

The methods of this invention are used to sustain a population of microorganisms in an aqueous fermentation broth used in a process to convert syngas to alcohol when the supply of syngas is decreased or ceased. The methods are particularly useful where the supply of syngas has ceased. The methods involve supplying at least one reducible anion in a rate an amount sufficient to maintain the population of microorganisms. In preferred aspects of this invention, the amount of at least one reducible anion is supplied continuously or intermittently to maintain a redox potential suitable for the microorganisms.

Syngas Bioconversions

Anaerobic fermentation to produce oxygenated organic compound uses a substrate (syngas) comprising at least one of (i) carbon monoxide and (ii) carbon dioxide and hydrogen, the latter being for the hydrogen conversion pathway. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas.

Syngas is typically produced by a gasifier. Any of the aforementioned biomass sources are suitable for producing syngas. The syngas produced thereby will typically contain from 10 to 60 mole % CO, from 10 to 25 mole % $CO_2$ and from 10 to 75, often at least about 30, and preferably between about 35 and 65, mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing and from industrial processes. These gases may have substantially different compositions than typical syngas, and may be essentially pure hydrogen or essentially pure carbon monoxide. The gas substrate may be obtained directly from gasification or from petroleum and petrochemical processing or industrial processes or may be obtained by blending two or more streams. Also, the gas substrate may be treated to remove or alter the composition including, but not limited to, removing components by chemical or physical sorption, membrane separation, and selective reaction.

The alcohol produced by the bioconversion of syngas will depend upon the microorganism or combination of microorganisms used for the fermentation and the conditions of the fermentation. Bioconversions of CO and $H_2/CO_2$ to n-butanol, propanol, ethanol and other alcohols are well known. For example, a concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. Published Patent Application 20070275447, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA- 10522 described in U.S. Pat. No. 8,143,037.

The aqueous fermentation broth will comprise an aqueous suspension of microorganisms and various media supplements. Suitable microorganisms generally live and grow under anaerobic conditions, meaning that dissolved oxygen is essentially absent from the fermentation broth. The various adjuvants to the aqueous fermentation broth may comprise buffering agents, trace metals, vitamins, salts etc. Adjustments in the fermentation broth may induce different conditions at different times such as growth and non-growth conditions which will affect the productivity of the microorganisms. U.S. Pat. No. 7,704,723 discloses the conditions and contents of suitable aqueous fermentation broth for bioconversion CO and $H_2/CO_2$ using anaerobic microorganisms.

Mixed cultures of anaerobic microorganisms can also be used for the bioconversions of syngas to product oxygenated organic compounds. See, for instance, U.S. patent application Ser. No. 13/802,916, filed Mar. 14, 2013, entitled Method For Production Of N-Propanol And Other C3-Carbon Containing Products From Syngas By Symbiotic Arrangement Of C1-Fixing And C3-Producing Anaerobic Microorganism Cultures (Toby, et al.); Ser. No. 13/802,930, filed Mar. 14, 2013, entitled Method For Production Of N-Propanol And/Or Ethanol By Fermentation Of Multiple Substrates In A Symbiotic Manner (Enzein, et al.); Ser. No. 13/802,924, filed Mar. 14, 2013, entitled Method For Production Of N-Propanol And Other C3-Containing Products From Syngas Using Membrane Supported Bioreactor (Datta, et al.) and Ser. No. 13/802,905, filed Mar. 14, 2013, entitled Method For Production Of N-Propanol And Other C3-Containing Products From Syngas By Symbiotic Co-Cultures Of Anaerobic Microorganisms (Datta, et al.). C1-fixing microorganisms include, without limitation, homoacetogens such as *Clostridium ljungdahlii*, *Clostridium autoethanogenum*, *Clostridium ragsdalei*, and *Clostridium coskatii*. Additional C1-fixing microorganisms include *Alkalibaculum bacchi*, *Clostridium thermoaceticum*, and *Clostridium aceticum*. Symbiotic C3-producing microorganisms capable of growing on ethanol and/or acetate as their primary carbon source include, but are not limited to, *Pelobacter propionicus*, *Clostridium neopropionicum*, *Clostridium propionicum*, *Desulfobulbus propionicus*, *Syntrophobacter wolinii*, *Syntrophobacter pfennigii*, *Syntrophobacter fumaroxidans*, *Syntrophobacter sulfatireducens*, *Smithella propionica*, *Desulfotomaculum thermobenzoicum* subspecies *thermosymbioticum*, *Pelotomaculum thermopropionicum*, and *Pelotomaculum schinkii*. Pathways for the production of product oxygenated organic compounds having three carbons include, but are not limited to, *Propionibacterium* species (*Propionibacterium acidipropionici*, *Propionibacterium acnes*, *Propionibacterium cyclohexanicum*, *Propionibacterium freudenreichii*, *Propionibacterium freudenreichii shermanii*, *Propionibacterium pentosaecum*) and several other anaerobic bacteria such as *Desulfobulbus propionicus*, *Pectinatus frisingensis*, *Pelobacter propionicus*, *Veillonella*, *Selenomonas*, *Fusobacterium*, *Bacteroides fragile*, *Prevotella ruminicola*, *Megasphaera elsdenii*, *Bacteroides vulgates*, and *Clostridium*, in particular *Clostridium propionicum*.

The aqueous broth is maintained under anaerobic fermentation conditions including a suitable temperature, say, between 25° C. and 60° C., frequently in the range of about 30° to 40° C. The conditions of fermentation, including the density of microorganisms and aqueous fermentation broth composition are preferably sufficient to achieve the sought conversion efficiency of hydrogen and carbon monoxide. The pH of the aqueous broth is acidic, often between about 4 and 6.5. The aqueous fermentation broth typically has a redox potential of less than about −250, preferably between about −250 and −520, millivolts.

The rate of supply of the feed gas under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous fermentation broth and the fermentation conditions. As the rate of transfer of carbon monoxide and hydrogen to the aqueous fermentation broth is a parameter for operation, conditions affecting the rate of transfer such as interfacial surface area between the gas and liquid phases and driving forces are important.

The bioreactor assembly may comprise one or more bioreactors which may be, with respect to gas flow, in parallel or in series flow. Each bioreactor may be of any suitable design; however, preferably the design and operation provides for a high conversion of carbon monoxide and hydrogen to oxygenated organic compound. Fermentation reactors include, but are not limited to, bubble column reactors; jet loop reactors; stirred tank reactors; trickle bed reactors; biofilm reactors including, but not limited to membrane bioreactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

The substrate depleted gas phase egressing from the aqueous fermentation broth will contain a small fraction of the hydrogen and carbon oxides introduced into the bioreactor assembly as the feed gas. Inerts such as nitrogen and primarily methane will comprise a portion of the depleted gas phase where syngas from steam reforming or oxygen-fed, autothermal reforming, especially steam or autothermal reforming of methane-containing gas, is used. The depleted gas phase may also contain sulfur-containing compounds, alcohol and the like volatilized from the aqueous fermentation broth.

The bioreactor may have added from time to time or continuously one or more streams of water, nutrients or adjuvants, and microorganisms. A portion of the aqueous fermentation broth is withdrawn from time to time or continuously from the bioreactor for product recovery. Product recovery can consist of known equipment arrangements for removal of residual cell material, separation and recovery of liquid products from the fermentation liquid, return of recovered fermentation liquid and purging of waste streams and materials. Suitable equipment arrangements can include filters, centrifuges, cyclones, distillation columns, membrane systems and other separation equipment. U.S. Pat. No. 8,211,679 shows an arrangement for a product recovery bioreactor that recovers an ethanol product from a bioreactor.

Impairment of Syngas Supply

Since the population of microorganisms can be maintained for short periods of time even with as little as 20 or 30 percent of the normal flow of syngas to the aqueous fermentation broth, in some instances the methods of this invention may not be implemented unless a loss of at least 70 or 80 percent of the normal syngas will be incurred or the duration of the impairment is anticipated to be lengthy, e.g., more than about 6 or 12 hours. The methods of this invention provide for the sustenance of the population of microorganisms even in the event of a total loss of syngas feed to the fermentation broth.

The fermentation broth, at the time of the decrease or cessation of the syngas flow, will contain alcohol and dissolved syngas. With a planned impairment of syngas supply, preparation for the supply of the at least one reducible anion can be in place, whereas with an unplanned impairment of syngas supply, time may be required to commence the supply of the at least one reducible anion. In either event, preferably within about 2, more preferably within about 0.5, hours of an occurrence of an impairment of syngas supply, the supply of the at least one reducible anion to the fermentation broth is commenced.

The fermentation broth will also contain alcohol produced by the bioconversion of syngas. The concentration of alcohol will depend upon the process conditions used for the bioconversion of syngas. Hence, the concentration of alcohol in the fermentation broth can vary over a wide range. Frequently, the concentration of alcohol in the fermentation broth is between about 0.2 to 5, say, about 0.5 to 3, volume percent. The fermentation broth will also contain other nutrients which will be available to the microorganisms during the period of impairment of syngas supply. For longer term periods of impairment of syngas supply, the addition of one or more alcohols may be required as discussed above. Typically, any added alcohol, where required, is provided at a rate to maintain the alcohol concentration greater than about 0.1 volume percent, e.g., between about 0.2 and about 1, volume percent. Although higher concentrations can be used depending upon the tolerance of the microorganisms to the alcohol, such higher concentrations are not essential and entail additional costs.

The methods of this invention are useful where cocultures of microorganisms are used to make the sought alcohol. The homoacetogen can bioconvert the alcohol with the at least one reducible anion to the carboxylate and provide an electron source for the partner microorganism. For instance, propanol can be bioconverted to propionate by one type of microorganism, and the propionate can then be bioconverted to acetate by the partner microorganism.

The fermentation broth may be maintained at substantially the same temperature as that before the decrease or cessation of syngas feed in order to facilitate restart of the syngas bioconversion upon the syngas feed being restored. In other instances, it may be desired to reduce the temperature of the fermentation broth in order to reduce metabolic activity and thereby prolong the ability of the methods of this invention to sustain the microorganism population. Where the temperature is reduced, the reduction is typically in the range of about 5° to 25° C., and often in the range of about 10° to 20° C.

The at least one reducible anion is added to the fermentation broth in accordance with the method of this invention at a rate and in an amount sufficient to substantially maintain the microorganism population in the aqueous fermentation broth. Nitrate anion is a preferred reducible anion due to its low cost, effectiveness and ability to be reduced to ammonium cation which can be used as a nitrogen source by the microorganisms. In some instances, a sulfur-containing reducible anion is used in combination with nitrate anion. The sulfur-containing reducible anion provide sulfur nutrient to the microorganisms and can assist in maintaining a sought redox potential in the aqueous fermentation broth.

The reducible anion may be supplied in any convenient form to the fermentation broth which is treated in accordance with this invention. Typically the reducible anion is supplied as a solid to be dissolved in the aqueous fermentation broth or as a concentrated aqueous solution of dissolved reducible anion. Often a soluble salt or acid of the reducible anion or mixture thereof is used as the source of nitrate anion. Suitable salts include, but are not limited to, ammonium, alkali metal (preferably one or more of sodium, potassium and cesium), and alkaline earth (preferably calcium) salts. The use of reducible anion salts does not result in any significant lowering of the pH of the aqueous broth as the alcohol is bioconverted converted to a carboxyl salt as opposed to a free acid. However, the pH will tend to increase due to the reducible anion reduction reactions. Thus, an acid of the reducible anion may be used as all or a portion of the source of the reducible anion to downwardly adjust the pH, if required.

The reducible anion is added to the fermentation broth continuously or intermittently to sustain the population of microorganisms during the period of decrease or cessation of syngas feed. Preferably the rate of addition of the reducible anion is such that its concentration in the fermentation broth remains less than about 20 milligrams per liter. The rate of addition of the reducible anion also serves to maintain the redox potential of the aqueous fermentation broth within a predetermined range.

In some instances at least one terminal electron acceptor is continuously or intermittently added to the fermentation broth. Terminal electron acceptors include, but are not limited to, fumarate and dimethyl sulfoxide. Other adjuvants and nutrients, including micronutrients, can also be continuously or intermittently added to the fermentation broth.

The methods of this invention sustain the viability of the population of microorganisms during an impairment in syngas supply. The methods are particularly advantageous for relatively brief durations of impairment, e.g., between about 6 and 30, say, 6 and 12, hours, but due to the metabolic rate attenuation, longer durations of impairment of syngas supply can be addressed even when the temperature of the aqueous fermentation broth is maintained at temperatures used for the syngas bioconversion.

Upon the ability to restore the syngas feed to the aqueous fermentation broth, the transition from the addition of nitrate anion to resumption of normal syngas may be effected in any suitable manner. Usually, the rate of syngas feed is increased as the population of microorganisms increases. In most instances, it is preferred to reduce the rate of, or stop, the supply of nitrate anion prior to starting or increasing the flow rate of syngas to the aqueous fermentation broth. If needed, the redox potential and pH of the aqueous fermentation broth may be adjusted to enhance the bioconversion of syngas. If the aqueous fermentation broth was cooled to reduce metabolic activity, the temperature of the broth should be increased to the sought temperature either before, during or after the transition from nitrate anion to syngas.

It is claimed:

1. A method for sustaining a population of microorganisms for the bioconversion of syngas to alcohol contained in an aqueous fermentation broth in the event of a decrease or cessation of syngas feed to the fermentation broth being used for the bioconversion which broth contains said alcohol, said method comprising continuously or intermittently adding during the period of decreased or ceased syngas feed at least one reducible anion selected from the group consisting of nitrate, sulfite, bisulfite, thiosulfate and metabisulfite anion, to the fermentation broth at a rate sufficient to substantially maintain the microorganism population by the bioconversion of alcohol to carboxylate anion and reduction of the at least one reducible anion but below that which would adversely affect the microorganisms.

2. The process of claim 1 wherein the at least one reducible anion comprises nitrate anion.

3. The process of claim 2 wherein at least one other reducible sulfur-containing anion is continuously or intermittently added during the period of decreased or ceased syngas feed.

4. The process of claim 2 wherein the rate of addition of nitrate anion to the fermentation broth is less than about 0.25 grams per hour per liter of aqueous fermentation broth.

5. The process of claim 1 wherein the concentration of the at least one reducible anion is maintained below about 20 milligrams per liter).

6. A method for sustaining a population of microorganisms for the bioconversion of syngas to alcohol contained in an aqueous fermentation broth in the event of a decrease or cessation of syngas feed to the fermentation broth being used for the bioconversion which broth contains said alcohol, said method comprising continuously or intermittently adding during the period of decreased or ceased syngas feed at least one reducible anion selected from the group consisting of nitrate, sulfite, bisulfite, thiosulfate and metabisulfite anion, to the fermentation broth at a rate sufficient to substantially maintain the microorganism population by the bioconversion of alcohol to carboxylate anion and reduction of the at least one reducible anion but below that which would adversely affect the microorganisms;
wherein the at least one reducible anion comprises nitrate anion, at least one other reducible anion is continuously or intermittently added during the period of decreased or ceased syngas feed, and the other reducible anion is at least one of sulfite, bisulfite, metabisulfite and thiosulfate anion.

7. The method of claim 6 wherein the redox potential of the aqueous fermentation broth is maintained in the range of about −250 to −525 millivolts in part by the rates of addition of the other reducible anion.

* * * * *